United States Patent [19]
Wenstrom, Jr.

[11] Patent Number: 5,520,696
[45] Date of Patent: May 28, 1996

[54] BONE ANCHOR INSTALLATION TOOL

[75] Inventor: Richard F. Wenstrom, Jr., Attleboro, Mass.

[73] Assignee: Mitek Surgical Products, Inc., Westwood, Mass.

[21] Appl. No.: 312,892

[22] Filed: Sep. 27, 1994

[51] Int. Cl.⁶ .................................................. A61B 17/04
[52] U.S. Cl. ................. 606/104; 606/72; 606/75
[58] Field of Search ............................ 606/232, 72–75, 606/104

[56] References Cited

U.S. PATENT DOCUMENTS

| | | | |
|---|---|---|---|
| 4,898,156 | 2/1990 | Gatturna et al. | 606/72 |
| 5,002,550 | 3/1991 | Li | 606/232 |
| 5,192,303 | 3/1993 | Gatturna et al. | 606/232 |

*Primary Examiner*—Gary Jackson
*Attorney, Agent, or Firm*—Pandiscio & Pandiscio

[57] ABSTRACT

A bone anchor installation tool is provided comprising a body having a distal end surface and a proximal end surface. An axial passageway extends between the distal end surface and the proximal end surface, with the distal end of the axial passageway being sized to receive at least a portion of a bone anchor. A shaft is slidably disposed within the axial passageway. The shaft is adapted to move between (i) a first retracted position wherein the shaft's distal end surface is withdrawn sufficiently far into the interior of the axial passageway so as to allow at least a portion of a bone anchor to be received therein, and (ii) a second extended position wherein the shaft's distal end surface projects out of the distal end of the axial passageway. A peripheral rib is formed on the exterior surface of the body so as to be yieldably engaged by a rib engaging element connected to the shaft as the shaft moves from its first retracted position to its second extended position. In use, when the shaft is in its first retracted position, the interaction of the peripheral rib and the rib engaging element will prevent the shaft from moving into its second extended position until a sufficient distally-directed force is applied to the shaft so as to cause the rib engaging element to yield out of engagement with the peripheral rib.

10 Claims, 6 Drawing Sheets

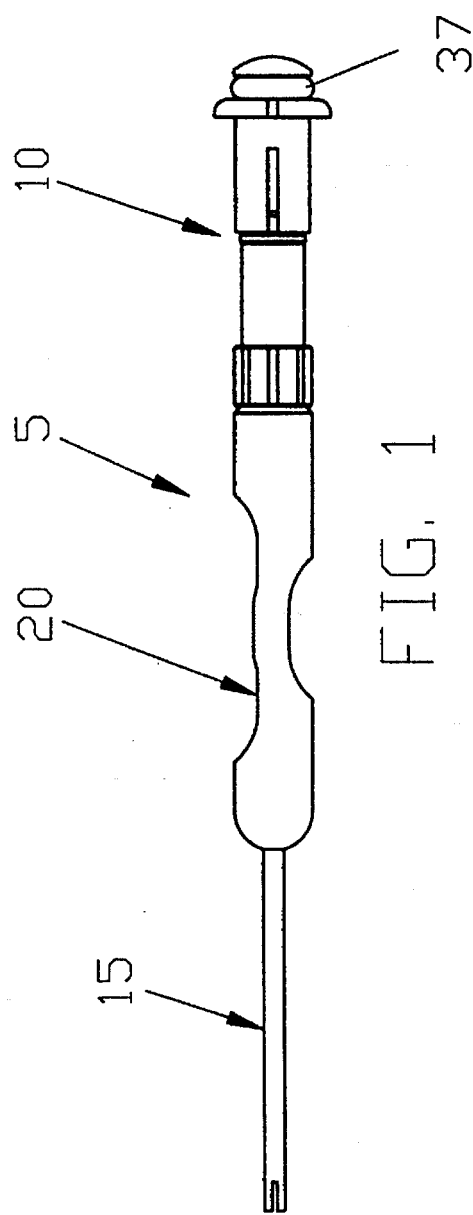
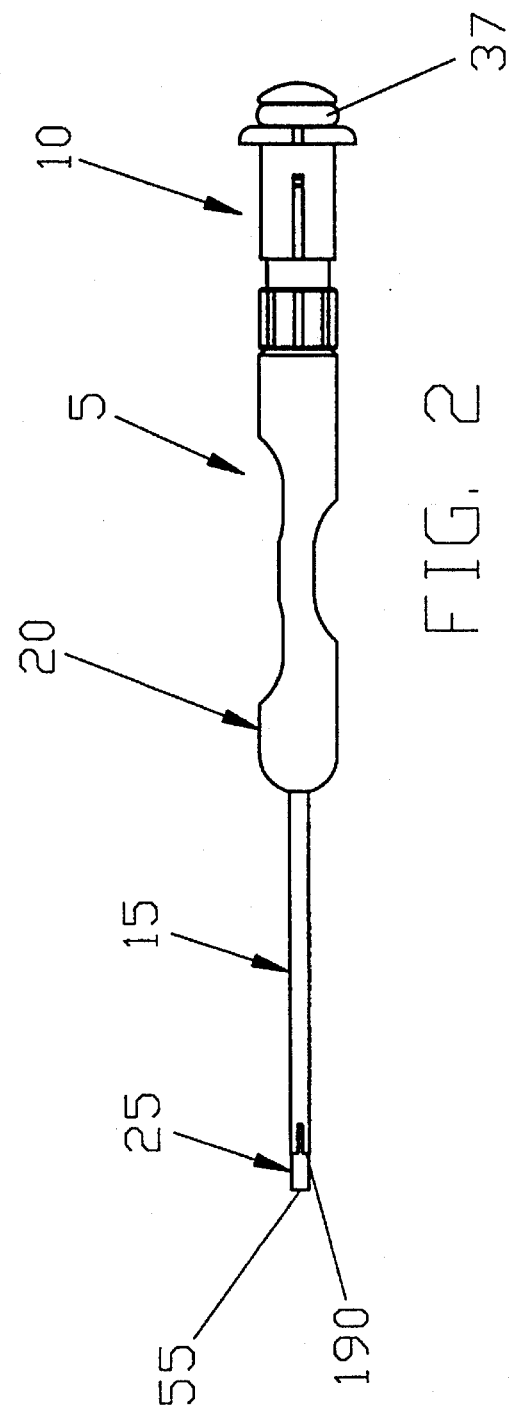
FIG. 1
FIG. 2

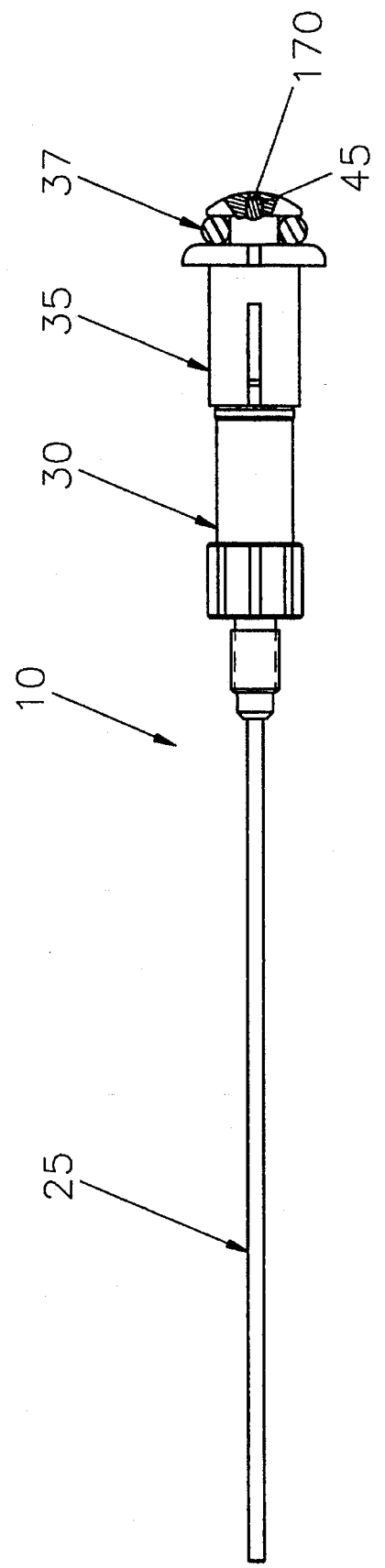

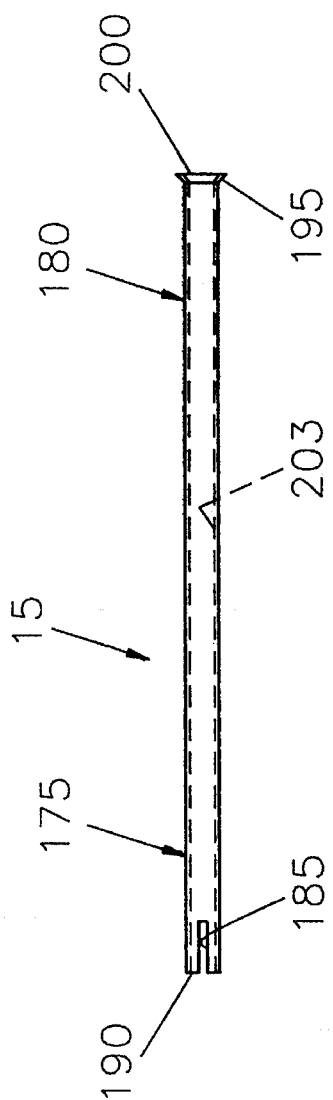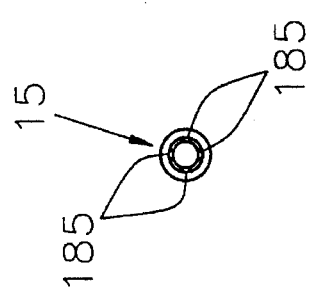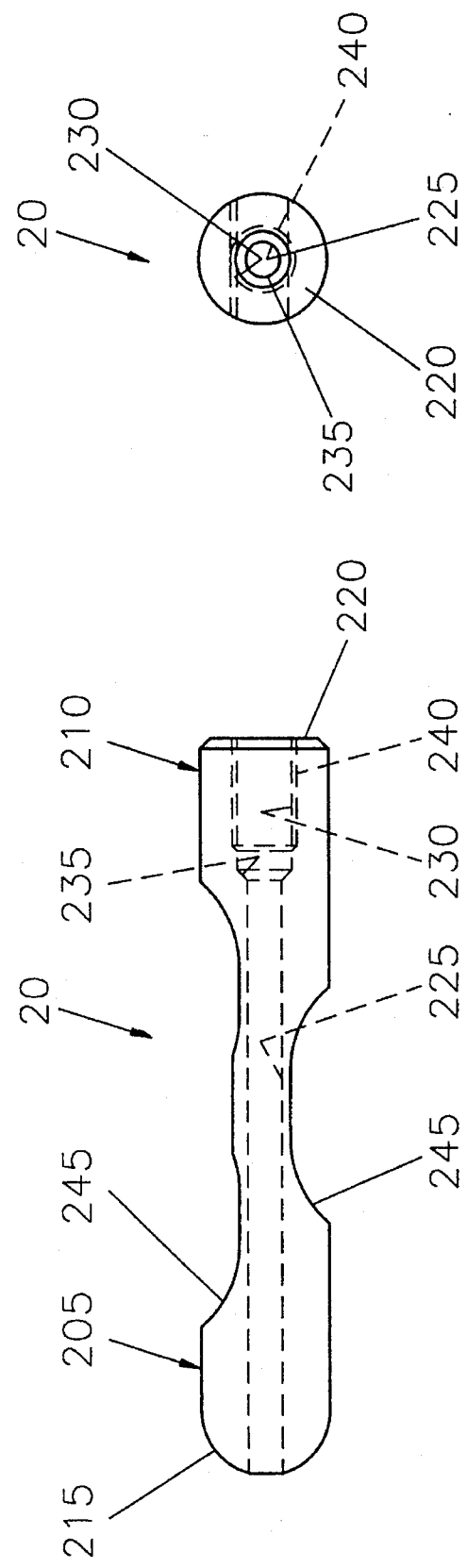

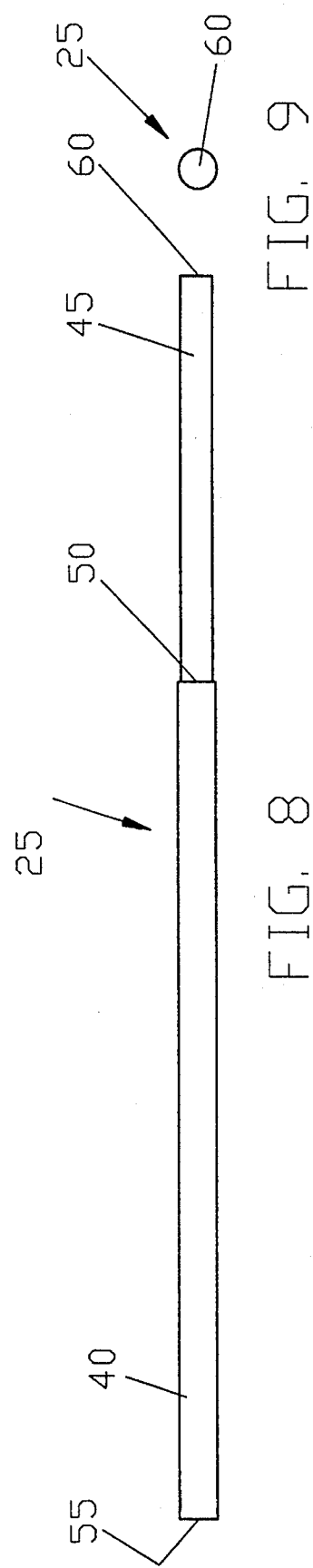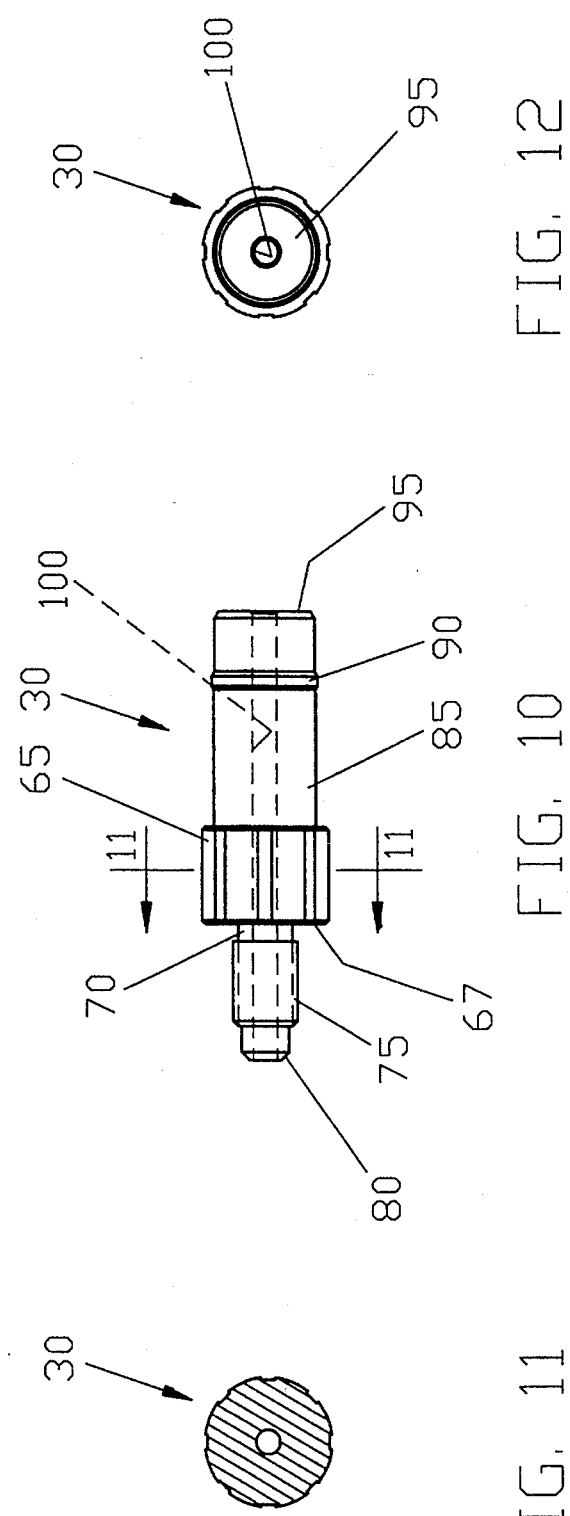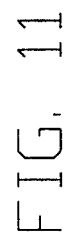

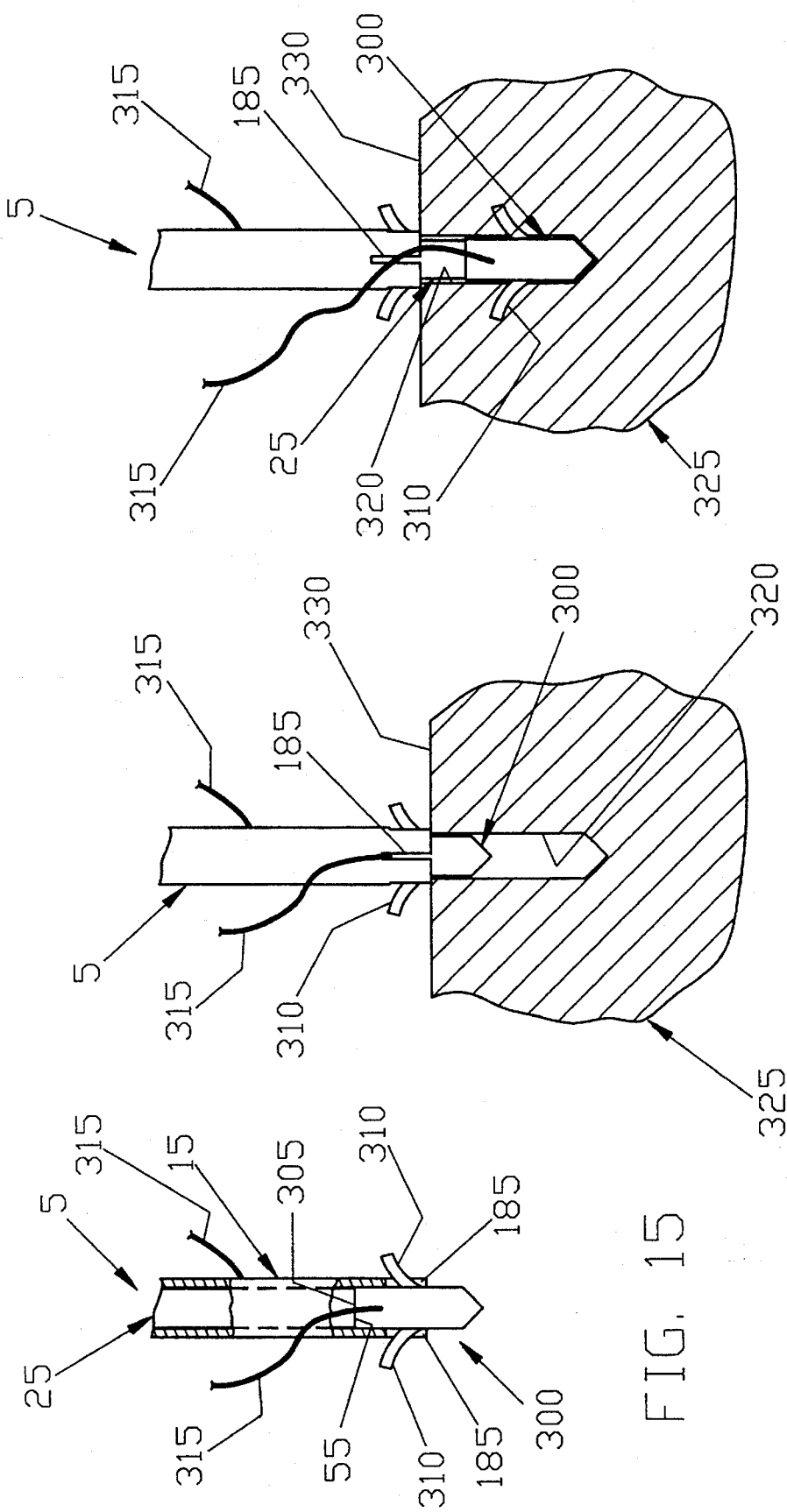

BONE ANCHOR INSTALLATION TOOL

FIELD OF THE INVENTION

This invention relates to surgical devices in general, and more particularly to devices for attaching suture, bone and/or soft tissue to bone.

BACKGROUND OF THE INVENTION

Bone anchors for attaching suture, bone and/or soft tissue to bone are well known in the art. See, for example, U.S Pat Nos. 4,898,156; 5,046,513; 5,192,303; 4,899,743; 4,968,315; 4,946,468; 5,002,550; 5,207,679; 5,217,486; 5,356,413; 5,358,511; and 5,372,599; and U.S. patent applications Ser. Nos. 08/075,168; 08/197,927; and 08/098,599.

Installation tools for deploying such bone anchors in bone are also well known in the art. See, for example, the foregoing U.S. patents and patent applications.

Complete details of the construction and operation of the foregoing exemplary bone anchors and bone anchor installation tools are provided in the above-identified patents and patent applications, which patents and patent applications are hereby incorporated herein by reference.

While the bone anchor installation tools disclosed in the foregoing U.S. patents and patent applications have proven more than satisfactory for most applications, it has been noted that certain problems can occur when using these installation tools in special situations.

More particularly, with some of the foregoing installation tools (e.g. the installation tools disclosed in U.S. Pat. Nos. 4,898,156; 5,046,513; 5,192,303; and 4,899,743), the portion of the tool which carries the anchor (i) is wider than the body of the anchor itself, and (ii) must be positioned within the bone during anchor deployment. As a result of this construction, the bone hole must be formed larger than the body of the anchor in order to permit anchor deployment. This can be a disadvantage in certain situations where it may be necessary to form the smallest possible hole in the bone.

With others of the foregoing installation tools (e.g. the installation tools disclosed in U.S. Pat. No. 5,217,486 and U.S. patent application Ser. No. 08/098,599), the portion of the tool which carries the anchor does not need to be received by the bone during anchor deployment. Instead, only a relatively thin drive pin enters the bone during anchor deployment. The drive pin is formed so that it has a diameter less than the diameter of the anchor body. As a result of this construction, the bone hole can be formed so that it has substantially the same width as the anchor body. However, it has also been found that where the installation tool is being used to set extremely small bone anchors, the drive pin must be so thin that it may bend or otherwise deform in certain circumstances. When this occurs, it may affect anchor deployment and/or render the installation tool unusable for subsequent anchor deployments.

In addition to the foregoing, it has also been found that where the installation tools are being used in conjunction with anchors adapted to attach suture to bone, it can be very helpful to provide suture management means for controlling the disposition of the one or more free suture ends. In this respect it is noted that with some of the foregoing installation tools (e.g. the installation tools disclosed in U.S. Pat. Nos. 4,946,468 and 5,002,550), such suture management means are provided. However, while such suture management means work well enough for most applications, it has been found that alternative suture management means could be helpful in some situations.

OBJECTS OF THE INVENTION

Accordingly, one object of the present invention is to provide an improved bone anchor installation tool.

Another object of the present invention is to provide an improved bone anchor installation tool, wherein the installation tool is adapted to deploy bone anchors of the type adapted to anchor suture to bone.

A further object of the present invention is to provide an improved bone anchor installation tool, wherein the installation tool is adapted to provide improved suture management means for managing the free end or ends of a suture or sutures attached to the bone anchor.

Yet another object of the present invention is to provide an improved bone anchor installation tool, wherein the installation tool is relatively easy to manufacture and relatively inexpensive to produce.

Still another object of the present invention is to provide a novel method for deploying a bone anchor in bone.

SUMMARY OF THE INVENTION

These and other objects of the present invention are achieved through the provision and use of a novel bone anchor installation tool.

In one form of the invention, the installation tool comprises:

a body having a distal portion and a proximal portion, the distal portion terminating in a distal end surface and the proximal portion terminating in a proximal end surface, and further wherein an axial passageway extends between the distal end surface and the proximal end surface, with the distal end of the axial passageway being sized to receive at least a portion of a bone anchor therein;

a shaft slidably disposed in the axial passageway, the shaft terminating in a distal end surface and being adapted to move between (i) a first retracted position wherein the shaft's distal end surface is withdrawn sufficiently far into the interior of the axial passageway so as to allow at least a portion of a bone anchor to be received within the distal end of the axial passageway, and (ii) a second extended position wherein the shaft's distal end surface projects out of the distal end of the axial passageway;

a peripheral rib formed on the exterior surface of the body; and rib engaging means connected to the shaft for yieldably engaging the peripheral rib as the shaft moves from its first retracted position to its second extended position, whereby when the shaft is in its first retracted position, the interaction of the peripheral rib and the rib engaging means will prevent the shaft from moving into its second extended position until a sufficient distally-directed force is applied to the shaft so as to cause the rib engaging means to yield out of engagement with the peripheral rib.

The installation tool also preferably comprises suture management means for managing a free end of a suture attached to a bone anchor disposed in the distal end of the axial passageway, the suture management means comprising a recess defining a first surface and an elastomer disposed in the recess so as to yieldably engage the first surface, whereby a free end of a suture may be forced between the first surface and the elastomer and retained there until thereafter forceably withdrawn.

In another form of the invention, the installation tool comprises:

a shaft comprising a first portion having a first cross-section, a second portion having a second cross-section less than the first cross-section, and a shoulder defined by the intersection of the first and second portions;

a shaft housing adapted to slidingly receive the shaft, the shaft housing having a proximal cylindrical portion including an annular rib positioned a predetermined distance from a proximal end thereof, a fluted finger grip, and a stem extending distally from the fluted finger grip, the stem including a threaded portion and terminating in a chamfered nose;

a shaft handle adapted to fixedly receive the proximal end of the shaft, the shaft handle comprising a slotted cylindrical portion having an inwardly facing lip disposed on a distal end thereof, the slotted cylindrical portion further including four slots, each of the slots being circumferentially positioned in spaced-apart opposing relation thereby defining four fingers adapted for gripping the annular rib of the shaft housing, a slotted flange disposed at a proximal end of the slotted cylindrical portion, the slotted flange having four slots each circumferentially disposed in spaced-apart opposing relation, and a T-shaped post extending from a proximal surface of the slotted flange and adapted for retaining a suture free end, the T-shaped post comprising a central column having a hole adapted for fixedly receiving the proximal end of the shaft and a flange disposed at a proximal end of the central column, the central column extending distally from a flat inner surface of the flange;

a rubber grommet disposed around the central column and adapted to releasably hold a length of suture attached to the suture anchor;

a sleeve comprising a flared proximal end, and a slotted distal end, the sleeve being adapted for slidingly receiving the shaft; and a sleeve handle comprising a proximal portion and terminating in a flat proximal end, a distal portion terminating in a rounded distal end, and a bore extending between the proximal end and the rounded distal end, the sleeve handle being adapted for slidingly receiving the sleeve, the proximal portion of the sleeve handle further including a threaded counterbore adapted for releasably fastening the threaded portion of the stem, the threaded counterbore forming an internal angled shoulder with a proximal end of the bore and adapted to receive the flared proximal end of the sleeve, the sleeve handle further including finger grip depressions disposed in opposing circumferential relation thereon and adapted to receive a thumb and fingers of a user during installation of the suture anchor.

The novel bone anchor installation tool can be used in the following manner to deploy a bone anchor into bone. First, the installation tool has its shaft positioned in its first retracted position. Next, a suture anchor is positioned at least partially within the distal end of the axial passageway, and the free end of a suture (attached to the suture anchor) is positioned between the aforementioned first surface and the elastomer. Then the distal end of the installation tool is positioned against the top surface of a bone having a hole formed therein, with the suture anchor being aligned with the hole. Next, the installation tool's shaft is moved from its first retracted position to its second extended position so as to deploy the suture anchor in the bone. Finally, the free end of the suture is removed from between the aforementioned first surface and the elastomer.

BRIEF DESCRIPTION OF THE DRAWINGS

These and other objects, features and advantages of the present invention will be more fully disclosed in, or rendered obvious by, the following detailed description of the preferred embodiment of the invention, which is to be considered together with the accompanying drawings wherein like numbers refer to like parts and further wherein:

FIG. 1 is a side elevational view of a fully assembled installation tool, wherein the installation tool's shaft is in its first retracted position;

FIG. 2 is a side elevational view of the same fully assembled installation tool, wherein the installation tool's shaft is in its second extended position;

FIG. 3 is a side elevational view, in partial section, of the installation tool's shaft subassembly;

FIG. 4 is a side elevational view of a sleeve which constitutes part of the installation tool;

FIG. 5 is an end view showing the distal end of the sleeve;

FIG. 6 is a side elevational view of a sleeve handle which constitutes part of the installation tool;

FIG. 7 is an end view showing the proximal end of the sleeve handle;

FIG. 8 is a side elevational view of a shaft which constitutes part of the installation tool's shaft subassembly;

FIG. 9 is an end view showing the proximal end of the shaft;

FIG. 10 is a side elevational view of a shaft housing which constitutes part of the installation tool's shaft subassembly;

FIG. 11 is a cross-sectional view taken along line 11—11 of FIG. 10;

FIG. 12 is an end view showing the proximal end of the shaft housing;

FIG. 15 is a side view partially in section showing a bone anchor installed in the distal end of the bone anchor installation tool of the present invention;

FIG. 16 is a side view partially in section showing the bone anchor and bone anchor installation tool of FIG. 16, wherein the distal end of the installation tool is in engagement with the outer surface of a bone and the bone anchor is about to be deployed in that bone; and FIG. 17 is a view like that of FIG. 16, except that the bone anchor has been deployed in the bone.

DETAILED DESCRIPTION OF THE PREFERRED EMBODIMENT

Figure 14:
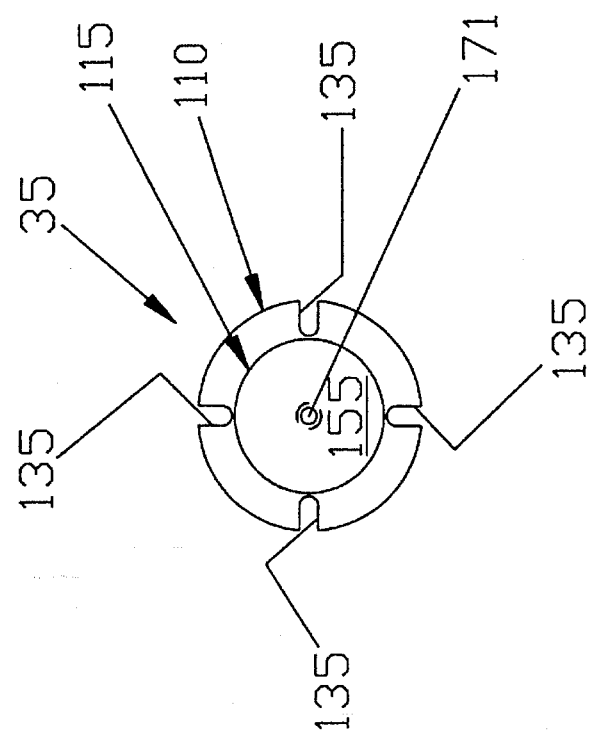
FIG. 14 is an end view showing the proximal end of the shaft handle.

Looking first at FIGS. 1 and 2, a bone anchor installation tool 5 is shown which comprises a preferred embodiment of the present invention. Installation tool 5 generally comprises a shaft subassembly 10 (FIGS. 1–3), a sleeve 15 (FIGS. 1, 2, 4 and 5) and a sleeve handle 20 (FIGS. 1, 2, 6 and 7).

More particularly, and looking now at FIG. 3, shaft subassembly 10 generally comprises a shaft 25, a shaft housing 30, a shaft handle 35 and a rubber grommet 37.

Shaft 25 is shown in greater detail in FIGS. 8 and 9. Shaft 25 comprises a first cylindrical portion 40 and a second cylindrical portion 45. Second cylindrical portion 45 has a smaller diameter than first cylindrical portion 40. First cylindrical portion 40 and second cylindrical portion 45 together define an annular shoulder 50. First cylindrical portion 40 terminates in a distal end surface 55. Second cylindrical portion 45 terminates in a proximal end surface 60.

Shaft housing 30 is shown in greater detail in FIGS. 10–12. Shaft housing 30 comprises a fluted finger grip 65 having a flat distal surface 67. A stem 70 extends distally away from the fluted finger grip's flat distal surface 67. Stem 70 includes a threaded portion 75 and terminates in a chamfered distal nose 80. Shaft housing 30 also comprises a cylindrical portion 85 extending proximally away from fluted finger grip 65. Cylindrical portion 85 includes an annular rib 90 and terminates in a flat proximal end surface 95. A central passageway 100 extends through shaft housing 30, from chamfered distal nose 80 of stem 70 to flat proximal end surface 95 of cylindrical portion 85.

Figure 13:
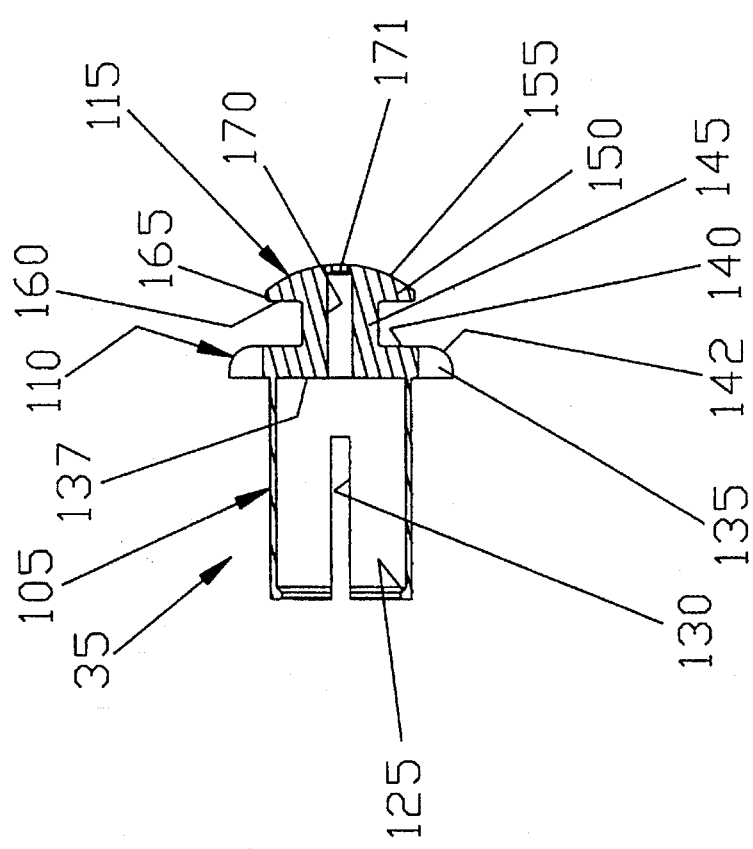
FIG. 13 is a side view in section of a shaft handle which constitutes part of the installation tool's shaft subassembly.

Shaft handle 35 is shown in greater detail in FIGS. 13 and 14. Shaft handle 35 comprises a slotted cylindrical portion 105, a slotted flange 110 and a T-shaped post 115. More particularly, slotted cylindrical portion 105 comprises an inwardly facing lip 125 and four slots 130. Slots 130 are disposed in equally-circumferentially-spaced relation about the circumference of slotted cylindrical portion 105. In essence, slots 130 divide slotted cylindrical portion 105 into four longitudinally-extending fingers. Slotted flange 110 comprises four slots 135. Slots 135 are disposed in equally-circumferentially-spaced relation about the circumference of slotted flange 110. Slots 135 of slotted flange 110 are aligned with slots 130 of slotted cylindrical portion 105. Slotted flange 110 terminates in a flat distal surface 137 and in a proximal surface 140. The flange's proximal surface 140 is preferably rounded somewhat at its circumferential edge 142, adjacent to where proximal surface 140 meets flat distal surface 137. T-shaped post 115 comprises a cylindrical central column 145 and an annular flange 150. Flange 150 terminates in a rounded proximal surface 155 and in a flat distal surface 160. A rounded circumferential edge 165 is defined by the intersection of rounded proximal surface 155 and flat distal surface 160. A hole 170 extends axially through slotted flange 110 and into T-shaped post 115, and communicates with the interior of slotted cylindrical portion 105. Hole 170 is coaxial with, and communicates with, another hole 171 which opens on rounded proximal surface 155.

Rubber grommet 37 (FIGS. 1–3) comprises a toroidal shaped piece of elastomer adapted to be positioned on shaft handle 35. More particularly, rubber grommet 37 is adapted to be fit over the shaft handle's cylindrical central column 145 so as to be compressed between flat proximal surface 140 of slotted flange 110 and flat distal surface 160 of annular flange 150.

Shaft subassembly 10 is assembled as follows. First, the shaft's second portion 45 is passed through the shaft housing's central passageway 100 until the shaft housing's chamfered distal nose 80 engages the shaft's annular shoulder 50. Then shaft handle 35 is passed over the proximal end of shaft housing 30 until the proximal end of shaft 25 enters the shaft handle's hole 170. The proximal end of shaft 25 is then made fast in hole 170 by welding, using access hole 171. On account of the foregoing construction, shaft 25 and shaft handle 35 thereafter operate as a single unit, with shaft housing 30 being slidably captured on shaft 25 between the shaft's annular shoulder 50 and the shaft handle's distal surface 137, as will hereinafter be described in further detail. Once this has been accomplished, rubber grommet 37 is then mounted onto the shaft handle's cylindrical central column 145.

Looking next at FIGS. 4 and 5, sleeve 15 comprises a distal portion 175 and a proximal portion 180. Distal portion 175 comprises four slots 185. Slots 185 are equally-circumferentially-spaced about the circumference of sleeve 15. Slots 185 open on the sleeve's distal end surface 190. The proximal portion of sleeve 15 is flared outwardly at 195 and terminates in a proximal end surface 200. A central passageway 203 extends between distal end surface 190 and proximal end surface 200.

Looking next at FIGS. 6 and 7, sleeve handle 20 comprises a distal portion 205 and a proximal portion 210. Distal portion 205 terminates in a rounded distal end surface 215 and proximal portion 210 terminates in a flat proximal end surface 220. Sleeve handle 20 also includes a bore 225 and a counterbore 230. Bore 225 opens on the sleeve handle's rounded distal end surface 215 and counterbore 230 opens on the sleeve handle's flat proximal end surface 220. Bore 225 and counterbore 230 meet at an internal angled shoulder 235. The proximal portion of counterbore 230 is threaded at 240. A plurality of finger grip depressions 245 are formed in the outer surface of sleeve handle 20.

The complete bone anchor installation tool 5 is assembled as follows. First, sleeve 15 is passed distal end first through counterbore 230 and bore 225 of sleeve handle 20, until the sleeve's flared portion 195 engages the sleeve handle's internal angled shoulder 235. Then the assembled shaft subassembly 10 is passed distal end first through counterbore 230 of sleeve handle 20 and central passageway 203 of sleeve 15, until chamfered distal nose 80 of shaft subassembly 10 enters counterbore 230 of sleeve handle 20. Shaft subassembly 10 is then rotated so that the shaft housing's threaded portion 75 engages threads 240 of sleeve handle 20. Shaft subassembly 10 is turned until the shaft housing's flat distal surface 67 engages the sleeve handle's proximal end surface 220. At this point, chamfered distal nose 80 of shaft subassembly 10 will make a close fit with proximal end surface 200 of sleeve 15, so as to maintain the longitudinal position of sleeve 15 relative to the remainder of the installation tool. At the same time, however, sleeve 15 is free to rotate relative to the remainder of the installation tool.

When bone anchor installation tool 5 is assembled in the foregoing manner, its shaft 25 will be free to move between (i) a first retracted position (FIG. 1) wherein the shaft's annular shoulder 50 is substantially in engagement with the shaft housing's chamfered distal nose 80, and the shaft handle's inwardly facing lip 125 is on the proximal side of, and substantially in engagement with, the shaft housing's annular rib 90, and the shaft's distal end surface 55 is withdrawn into the interior of sleeve 15; and (ii) a second extended position (FIG. 2) wherein the shaft handle's flat distal end surface 137 is in engagement with the shaft housing's flat proximal end surface 95, and the shaft handle's inwardly facing lip 125 is on the distal side of, and substantially displaced from, the shaft housing's annular rib 90, and the shaft's distal end surface 55 protrudes a substantial distance beyond the sleeve's distal end surface 190.

Bone anchor installation tool 5 is preferably used to deploy a suture anchor of the sort disclosed in the aforementioned U.S. Pat. No. 5,217,486 and/or a suture anchor of the sort disclosed in the aforementioned U.S. patent application Ser. No. 08/197,927, i.e., bone anchor installation tool 5 is preferably used to deploy a suture anchor of the sort comprising (i) a generally cylindrical body, (ii) a pair of flexible barbs extending laterally out of the side of the body, and (iii) suture attachment means for attaching a length of suture to the body. Of course, bone anchor installation tool 5 may also be used to deploy other types of bone anchors in bone or other types of fasteners in a workpiece, so long as such bone anchor or fastener is compatible with the present invention.

Bone anchor installation tool 5 is intended to be used as follows. First, installation tool 5 is positioned so that its shaft 25 is in its aforementioned first retracted position, wherein the shaft's annular shoulder 50 is substantially in engagement with the shaft housing's chamfered distal nose 80, and the shaft handle's inwardly facing lip 125 is on the proximal side of, and substantially in engagement with, the shaft housing's annular rib 90, and the shaft's distal end surface 55 is withdrawn into the interior of sleeve 15 (FIG. 1). It is to be appreciated that bone anchor installation tool 5 will be inclined to remain in its aforementioned first retracted position until it is thereafter forced to assume another position, inasmuch as the shaft housing's annular rib 90 will tend to inhibit passage of the shaft handle's inwardly facing lip 125.

Next, and looking now at FIG. 15, a suture anchor 300 is loaded into the distal end of sleeve 15 so that the suture anchor's proximal end 305 rests against the shaft's distal end surface 55, with the suture anchor's two barbs 310 extending out through two of the sleeve's slots 185 and the suture anchor's two lengths of suture 315 extending out through the other two of the sleeve's slots 185.

The two lengths of suture 315 are then extended tautly back along the length of the installation tool and threaded through one or more of the shaft handle's slots 135 before being wound tightly around the shaft handle's cylindrical central column 145, in the space between rubber grommet 37 and the shaft handle's surface 140. The resilient engagement of rubber grommet 37 with the shaft's surface 140 thereafter serves to keep the two lengths of suture 315 securely in place at the proximal end of the installation tool, yet allow a surgeon to easily pull the two lengths of suture free from the installation tool when needed. Furthermore, by ensuring that the two lengths of suture 315 extend tautly back along the length of installation tool 5 prior to being secured in place via rubber grommet 37, the two lengths of suture 315 will serve to ensure that suture anchor 300 cannot become prematurely disengaged from the distal end of the installation tool.

Next, and looking now at FIG. 16, the installation tool is manipulated so as to position the distal portion of suture anchor 300 within the top of a hole 320 formed in a bone 325, with the distal end of sleeve 15 engaging the top surface 330 of the bone.

Suture anchor 300 can then be deployed in bone 325 by pressing on the shaft handle's proximal surface 155 so as to urge the installation tool's shaft 25 into its aforementioned second extended position. As this occurs, the shaft handle's inwardly facing lip 125 will be forced over the shaft housing's annular rib 90 as the shaft handle's flat distal end surface 137 moves into engagement with the shaft housing's flat proximal end surface 95 and the shaft's distal end surface 55 moves out of the sleeve's distal end. As a consequence of this action, suture anchor 300 will be driven out of the distal end of sleeve 15 and into bone 325, with the suture anchor's barbs 310 securing the anchor in place and with the two lengths of suture 315 extending back out of the bone hole to the installation tool. The two lengths of suture 315 may then be unwound from the installation tool before the installation tool is removed from the surgical site.

Advantges of the Present Invention

Numerous advantages are obtained by using the present invention.

For one thing, an improved bone anchor installation tool is provided.

For another thing, an improved bone anchor installation tool is provided, wherein the installation tool is adapted to deploy bone anchors of the type adapted to anchor suture to bone.

Also, an improved bone anchor installation tool is provided, wherein the installation tool is adapted to provide improved suture management means for managing the free end or ends of a suture or sutures attached to the bone anchor.

Furthermore, an improved bone anchor installation tool is provided, wherein the installation tool is relatively easy to manufacture and relatively inexpensive to produce.

In addition, an improved method is provided for deploying a bone anchor in bone.

Still other advantages of the invention will be obvious to those skilled in the art.

Modifications of the Preferred Embodiment

It will, of course, be appreciated that certain modifications may be made to the foregoing preferred embodiment of the present invention without departing from the scope of the present invention.

Thus, for example, more than four slots 185 may be provided in the distal end of sleeve 15, where the installation tool is to be used in conjunction with a bone anchor of the sort having more than two barbs and/or more than two free suture ends.

Furthermore, more or less than four slots 130 may be provided in slotted cylindrical portion 105, and/or more or less than four slots 135 may be provided in slotted flange 110.

Also, fluted finger grip 65 could be formed with an exterior surface which is knurled rather than fluted, or finger grip 65 could be formed with a relatively smooth surface if desired.

Additionally, suture could be held to the proximal end of the installation tool by wrapping it around cylindrical central column 145 between rubber grommet 37 and the shaft handle's flat surface 160, rather than between rubber grommet 37 and the shaft handle's surface 140.

These and other changes will be obvious to a person skilled in the art, and are considered to be within the scope of the present invention.

What is claimed is:

1. An installation tool for deploying a bone anchor in bone, said installation tool comprising:

a body having a distal portion and a proximal portion, said distal portion terminating in a distal end surface and said proximal portion terminating in a proximal end surface, and further wherein an axial passageway extends between said distal end surface and said proximal end surface, with said distal end of said axial passageway being sized to receive at least a portion of a bone anchor therein;

a shaft slidably disposed in said axial passageway, said shaft terminating in a distal end surface and being adapted to move between (i) a first retracted position wherein said shaft's distal end surface is withdrawn sufficiently far into the interior of said axial passageway so as to allow at least a portion of a bone anchor to be received within said distal end of said axial passageway, and (ii) a second extended position wherein said shaft's distal end surface projects out of said distal end of said axial passageway;

a peripheral rib formed on the exterior surface of said body; and rib engaging means connected to said shaft for yieldably engaging said peripheral rib as said shaft moves from its said first retracted position to its said second extended position, whereby when said shaft is in its said first retracted position, the interaction of said peripheral rib and said rib engaging means will prevent said shaft from moving into its said second extended position until a sufficient distally-directed force is applied to said shaft so as to cause said rib engaging means to yield out of engagement with said peripheral rib.

2. An installation tool according to claim 1 wherein said installation tool further comprises suture management means for managing a free end of a suture attached to a bone anchor disposed in said distal end of said axial passageway, said suture management means comprising a recess defining a first surface and an elastomer disposed in said recess so as to yieldably engage said first surface, whereby a free end of a suture may be forced between said first surface and said elastomer and retained there until thereafter forceably withdrawn.

3. An installation tool for deploying a suture anchor, said installation tool comprising:

a shaft comprising a first portion having a first cross-section, a second portion having a second cross-section less than said first cross-section, and a shoulder defined by the intersection of said first and said second portions;

a shaft housing adapted to slidingly receive said shaft, said shaft housing having a proximal cylindrical portion including an annular rib positioned a predetermined distance from a proximal end thereof, a fluted finger grip, and a stem extending distally from said fluted finger grip, said stem including a threaded portion and terminating in a chamfered nose;

a shaft handle adapted to fixedly receive said proximal end of said shaft, said shaft handle comprising a slotted cylindrical portion having an inwardly facing lip disposed on a distal end thereof, said slotted cylindrical portion further including four slots, each of said slots being circumferentially positioned in spaced-apart opposing relation thereby defining four fingers adapted for gripping said annular rib of said shaft housing, a slotted flange disposed at a proximal end of said slotted cylindrical portion, said slotted flange having four slots each circumferentially disposed in spaced-apart opposing relation, and a T-shaped post extending from a proximal surface of said slotted flange and adapted for retaining a suture free end, said T-shaped post comprising a central column having a hole adapted for fixedly receiving said proximal end of said shaft and a flange disposed at a proximal end of said central column, said central column extending distally from a flat inner surface of said flange; and a rubber grommet disposed around said central column and adapted to releasably hold a length of suture attached to said suture anchor;

a sleeve comprising a flared proximal end a slotted distal end, said sleeve adapted for slidingly receiving said shaft; and a sleeve handle comprising a proximal portion and terminating in a flat proximal end, a distal portion terminating in a rounded distal end, and a bore extending between said proximal end and said rounded distal end, said sleeve handle being adapted for slidingly receiving said sleeve, said proximal portion of said sleeve handle further including a threaded counterbore adapted for releasably fastening said threaded portion of said stem, said threaded counterbore forming an internal angled shoulder with a proximal end of said bore and adapted to receive said flared proximal end of said sleeve, said sleeve handle further including finger grip depressions disposed in opposing circumferential relation thereon and adapted to receive a thumb and fingers of a user during installation of said suture anchor.

4. An installation tool according to claim 3 wherein said shaft's first and second cross-sections are cylindrical.

5. An installation tool according to claim 3 wherein said fluted finger grip comprises a plurality of circumferentially disposed flutes.

6. An installation tool according to claim 3 wherein said slotted flange comprises four slots, each of said slots being circumferentially positioned in spaced-apart opposing relation with each other and in aligned relation to said slots in said slotted cylindrical portion of said shaft handle.

7. An installation tool according to claim 3 wherein said flange of said shaft handle further comprises a rounded proximal surface and a flat distal surface so as to define a rounded circumferential edge therebetween.

8. An installation tool according to claim 3 wherein said proximal end of said shaft is welded in said hole of said shaft handle.

9. A system for deploying a suture anchor in a hole formed in a bone, said system comprising:

(i) a suture anchor comprising a generally cylindrical housing, a pair of flexible barbs extending laterally out of the side of said housing, and suture attachment means for attaching a length of suture to said housing; and (ii) an installation tool for deploying said suture anchor in bone, said installation tool comprising:

a body having a distal portion and a proximal portion, said distal portion terminating in a distal end surface and said proximal portion terminating in a proximal end surface, and further wherein an axial passageway extends between said distal end surface and said proximal end surface, with said distal end of said axial passageway being sized to receive at least a portion of said suture anchor therein;

a shaft slidably disposed in said axial passageway, said shaft terminating in a distal end surface and being adapted to move between (i) a first retracted position wherein said shaft's distal end surface is withdrawn sufficiently far into the interior of said axial passageway so as to allow at least a portion of said suture anchor to be received within said distal end of said axial passageway, and (ii) a second extended position wherein said shaft's distal end surface projects out of said distal end of said axial passageway;

a peripheral rib formed on the exterior surface of said body;

rib engaging means connected to said shaft for yieldably engaging said peripheral rib as said shaft moves from its said first retracted position to its said second extended position, whereby when said shaft is in its said first retracted position, the interaction of said peripheral rib and said rib engaging means will prevent said shaft from moving into its said second extended position until a sufficient distally-directed force is applied to said shaft so as to cause said rib engaging means to yield out of engagement with said peripheral rib; and suture management means for managing a free end of a suture attached to said suture anchor when said suture anchor is disposed in said distal end of said axial passageway, said suture management means comprising a recess defining a first surface and an elastomer disposed in said recess so as to yieldably engage said first surface, whereby a free end of a suture may be forced between said first surface and said elastomer and retained there until thereafter forceably withdrawn.

10. A method for deploying a bone anchor in bone, said method comprising the steps of:

(1) providing a system for deploying a suture anchor in a hole formed in a bone, said system comprising:

(i) a suture anchor comprising a generally cylindrical housing, a pair of flexible barbs extending laterally out of the side of said housing, and suture attachment means for attaching a length of suture to said housing; and (ii) an installation tool for deploying said suture anchor in bone, said installation tool comprising:

a body having a distal portion and a proximal portion, said distal portion terminating in a distal end surface and said proximal portion terminating in a proximal end surface, and further wherein an axial passageway extends between said distal end surface and said proximal end surface, with said distal end of said axial passageway being sized to receive at least a portion of said suture anchor therein;

a shaft slidably disposed in said axial passageway, said shaft terminating in a distal end surface and being adapted to move between (i) a first retracted position wherein said shaft's distal end surface is withdrawn sufficiently far into the interior of said axial passageway so as to allow at least a portion of said suture anchor to be received within said distal end of said axial passageway, and (ii) a second extended position wherein said shaft's distal end surface projects out of said distal end of said axial passageway;

a peripheral rib formed on the exterior surface of said body;

rib engaging means connected to said shaft for yieldably engaging said peripheral rib as said shaft moves from its said first retracted position to its said second extended position, whereby when said shaft is in its said first retracted position, the interaction of said peripheral rib and said rib engaging means will prevent said shaft from moving into its said second extended position until a sufficient distally-directed force is applied to said shaft so as to cause said rib engaging means to yield out of engagement with said peripheral rib; and suture management means for managing a free end of a suture attached to said suture anchor when said suture anchor is disposed in said distal end of said axial passageway, said suture management means comprising a recess defining a first surface and an elastomer disposed in said recess so as to yieldably engage said first surface, whereby a free end of a suture may be forced between said first surface and said elastomer and retained there until thereafter forceably withdrawn;

(2) positioning said shaft in its said first retracted position;

(3) positioning a suture anchor at least partially within said distal end of said axial passageway, and positioning the free end of a suture attached to said said suture anchor between said first surface and said elastomer;

(4) positioning said distal end of said installation tool against the top surface of a bone having a hole formed therein, with said suture anchor being aligned with said hole;

(5) moving said shaft from its said first retracted position to its said second extended position so as to deploy said suture anchor in said bone; and (6) removing said free end of said suture attached to said suture anchor from between said first surface and said elastomer.

* * * * *